(12) United States Patent
Gilman

(10) Patent No.: US 6,870,074 B2
(45) Date of Patent: Mar. 22, 2005

(54) THIN FILM SCAR DRESSING AND USE THEREOF

(75) Inventor: Thomas H. Gilman, Spring Grove, IL (US)

(73) Assignee: Hollister Incorporated, Libertyville, IL (US)

( * ) Notice: Subject to any disclaimer, the term of this patent is extended or adjusted under 35 U.S.C. 154(b) by 54 days.

(21) Appl. No.: 10/439,810

(22) Filed: May 16, 2003

(65) Prior Publication Data

US 2003/0220597 A1 Nov. 27, 2003

Related U.S. Application Data

(60) Provisional application No. 60/382,908, filed on May 23, 2002.

(51) Int. Cl.[7] .................................................. A61F 13/00
(52) U.S. Cl. .............................. 602/52; 604/42; 604/43; 604/54
(58) Field of Search ............................... 602/41–43, 52, 602/54, 48, 57–59; 128/888, 889; 429/443, 449

(56) References Cited

U.S. PATENT DOCUMENTS

| 1,476,894 A | | 12/1923 | Judd ........................... 602/52 |
| 5,522,794 A | * | 6/1996 | Ewall .......................... 602/41 |
| 5,891,076 A | | 4/1999 | Fabo ........................... 602/52 |
| 5,895,656 A | | 4/1999 | Hirshowitz et al. ......... 424/402 |
| 6,346,653 B1 | | 2/2002 | Sessions et al. .............. 602/42 |
| 2002/0038099 A1 | | 3/2002 | Griffiths et al. |

FOREIGN PATENT DOCUMENTS

| EP | 0 236 104 | 9/1987 |
| WO | WO 01/91681 | 12/2001 |

* cited by examiner

*Primary Examiner*—Kim M. Lewis
(74) *Attorney, Agent, or Firm*—Marshall, Gerstein & Borun LLP

(57) ABSTRACT

A scar dressing of thin polymeric film having a thickness no greater than about 10 mils (0.254 mm) is disclosed. The film is preferably coated on one side with a hypoallergenic pressure-sensitive adhesive, and the dressing as a whole has a permeability profile for moisture vapor and oxygen that renders the dressing particularly suitable for treating scar tissue, particularly where the scarring has become, or may become, hypertropic or keloidal.

16 Claims, No Drawings

THIN FILM SCAR DRESSING AND USE THEREOF

RELATED APPLICATION

This application claims priority from U.S. Provisional Patent application Ser. No. 60/382,908, filed May 23, 2002.

BACKGROUND AND SUMMARY

Hypertrophic scarring is a condition that sometimes develops after a wound has healed and is recovered with new epithelium. Tissue builds under the new epithelium to a level above the normal skin level, resulting in a scar that is raised. It is also often red, puritic, and painful.

Distinguishing keloids from hypertrophic scars can be difficult. Clinically, keloids can be distinguished from hypertrophic scars in that keloids extend beyond the original wound and rarely regress, whereas hypertrophic scars remain within the confines of the original wound and often spontaneously regress. Both keloids and hypertrophic scars are abnormal wound responses and result from a connective tissue response to trauma, inflammation, surgery, or burns and occasionally seem to occur spontaneously. Both are characterized by the abundant deposition of collagen and glycoprotein.

A therapy that has proven effective in reducing these unwanted characteristics of keloids and hypertrophic scars is silicone sheet therapy. In such therapy, the scar is covered with a sheet of silicone rubber about 140 mil (3.5 mm) thick or, in some reports, about 70 mil (1.75 mm) thick. The scar should be covered for 12 hours per day or more, for a period of at least 8 weeks. If such regimen is followed, existing scars have been found to improve. This treatment has also been shown to be effective as a prophylactic, reducing the incidence of hyprotrophic scars after surgery.

While silicone gel sheeting is now recognized for its effectiveness in preventing the formation of hypertrophic scars and keloids, and for treating existing scars and keloids, the mechanism for its efficacy has remained a mystery and continues to be debated. The medical literature is devoid of an explanation for its effectiveness. Medical investigators have excluded pressure, oxygen tension, temperature and silicone absorption in the skin as possible explanations for its action. Quinn K J, Evans J H, Courtney J M, Gaylor J D, Reid W H (1985), Non-pressure treatment of hypertrophic scars, Burns Incl. Therm. Inj. 12:102–8; Quinn KJ (1987), Silicone gel in scar treatment, Burns Incl. Therm. Inj. S33–40.

The problem with silicone sheet therapy is that it can be difficult to keep the sheet in place over a scar. Silicone sheets that are mildly adhesive have been developed, but these also have problems with staying in place. A preferred time for treatment is while sleeping, but then the sheet can be easily dislodged without the patient's knowledge and therapy is not provided as a result. One reason such a sheet may become dislodged is its substantial thickness, presenting the possibility that such a sheet may be easily caught on a bedsheet or pillow. Silicone tape is often used to hold such a sheet in place, but such tape is relatively expensive compared to conventional medical tapes, the latter being unuseable because they do not stick to silicone gel sheet.

A main aspect of this invention lies in discovering the reasons for the effectiveness of silicone gel sheeting and, based on that discovery, providing a relatively thin film dressing that has critical characteristics identical or similar to those of a silicone gel dressing. Because the dressing of this invention utilizes a film that is thin, flexible and highly conformable, the problems associated with the use of silicone gel sheeting are avoided.

Because of its thinness and flexibility, a dressing of this invention will stay in place much better than currently available silicone dressings. It can be made with less expensive materials and held in place with less expensive tapes. In a preferred embodiment of the invention, the dressing is self-adhesive—that is, it has a coating on one side of a hypoallergenic pressure-sensitive adhesive, thereby increasing patient convenience and providing an added level of stay-in-place performance. The dressing of this invention is also more conformable and less visible or detectable than currently-available dressings intended for the same therapy. Since a dressing should be worn 12 hours or more each day for a period of at least 8 weeks, such advantages are of particular importance to users.

Briefly, the thin film dressing of this invention takes the form of a flexible and anatomically conformable polymeric film having a thickness no greater than about 10 mil (0.254 mm). Such film should have a moisture vapor transmission rate (MVTR) less than that of skin, generally no greater than 15 milligrams per square centimeter per day, and an oxygen transmission rate of at least 300 cubic centimeters per 100 square inches per day. Preferably the MVTR should be 1 to 10 $mg/cm^2/day$ and more preferably 4 to 8 $mg/cm^2/day$. As to the oxygen transmission rate, it is preferable that the film have a transmission rate at least 600 cc/100 $in^2/day$, and more preferably at least 2000 cc/100 $in^2/day$.

The thin film is preferably coated on one side with a medical-grade hypoallergenic pressure-sensitive adhesive to facilitate application and retention of the dressing over a wound site. The film and/or its adhesive coating may also be formulated to include a suitable bacteriostatic or microbicidal agent to prevent or reduce skin rashes that might otherwise occur during use of the thin film scar dressing of this invention.

The invention also involves the method of use of such a dressing. Such method is directed to the treatment of dermal wounds for reducing scars and their formation, and involves the step of covering, and preferably adhering, the thin film dressing of this invention to the treatment area. For optimal effectiveness, such a dressing should be worn 12 hours or more each day for a period of at least 8 weeks.

DETAILED DESCRIPTION OF PREFERRED EMBODIMENT

The mechanism responsible for the effectiveness of a thin film dressing of this invention, with a thickness no greater than 10 mil (0.254 mm), has now been discovered by applicant to be the same as the previously unrecognized mechanism responsible for the effectiveness of relatively thick (140 mil, or 3.5 mm) silicone sheeting such as that previously supplied by Dow Corning Wright, and also CicaCare silicone sheeting (about 70 mil or 1.75 mm in thickness) of proven efficacy available from Smith and Nephew, Hull, England. All involve the right combination of water vapor permeability and oxygen permeability.

The water vapor permeability of a thin film dressing embodying this invention must be in a range that will limit the escape of water from the skin, producing hydration of the stratum corneum. Hydration of the stratum corneum is important because, among other things, it increases the oxygen permeability, a key to effective treatment of hypertrophic scars and keloids. To produce hydration of the stratum corneum, the transport of water through the dressing must be lower than the rate at which water is normally produced at the skin surface. The water vapor transmission rate of skin is known to be approximately 20 mg/cm$^2$/day (or 8.5 g/m$^2$/hour). Quinn K J, Evans J H, Courtney J M, Gaylor J D, Reid W H (1985), Non-pressure treatment of hypertrophic scars, Burns Incl. Therm. Inj. 12:102–8. On the other hand, water vapor permeability of the dressing preferably is not too low, because over-hydration could lead to growth of skin microorganisms and development of skin rashes under a dressing.

Specifically, the MVTR of a thin film dressing embodying this invention should be less than that of skin, and in general should be no greater than about 15 mg/cm2/day, with a preferred range being 1 to 10 mg/cm$^2$/day and a more preferred range being 4 to 8 mg/cm$^2$/day. By comparison, the CicaC are has an MVTR of about 7 mg/cm$^2$/day.

With regard to avoiding the development of skin rashes, a side effect that sometimes occurs with silicone sheet therapy as reported in the literature, the thin film wound dressing of this invention may include a bacteriostatic- or microbicidal agent in the film, or in the adhesive coating, or in both. An example would be to admix into the adhesive casting solution, or into the film melt or film casting solution, a fine powder of triclosan, an agent known for use in controlling skin flora. Other well-known microbicidal or bacteriostatic agents may be used, for example, silver and its salts, chlorhexidine, parachlorometaxylenol, triclocarban, and other agents having similar properties.

The oxygen permeability of a thin film dressing of this invention must be high because it is the combination of a hydrated stratum corneum and a high external oxygen tension that is understood to be responsible for the therapeutic effect. Medical literature indicates that low oxygen concentration at a wound site, producing tissue hypoxia, is important in promoting wound healing because it encourages capillary growth or angiogenesis. Conversely, when the concentration of oxygen in a wound chamber is high, capillary growth is arrested or inhibited. It has been postulated that the mechanism may be the effect of oxygen concentration on macrophages, the primary cells populating the dead space of a wound, and that hypoxic conditions enhance the release of growth factors from the macrophages, whereas such release is terminated when the oxygen level is raised. Knighton D R, Silver I A, Hunt, T K (1981), Regulation of Wound-Healing Angiogensis—Effect of Oxygen Gradients on Inspired Oxygen Concentration, Surgery, 90:262–70. While not wishing to be bound by a theoretical explanation, it is believed that the effectiveness of silicone sheeting in reducing hypertrophic scars and keloids, and the effectiveness of the thin film dressings of this invention, lies in increasing the oxygen concentration about a healed wound to inhibit microphage activity and thereby repress scar formation or induce regression of hypertrophic scars and keloids. Thus, in a thin film wound dressing embodying this invention, the oxygen permeability should be at least 300 cc/100 in$^2$/day, the preferred lower limit being at least 600 cc/100 in$^2$/day, and the more preferred or optimum lower limit being at least 2000 cc/100 in$^2$/day. In comparison, the CicaCare product has a measured oxygen permeability of about 2300 cc/100 in$^2$/day.

Preferably, a thin film dressing embodying this invention is adhesive, that is, the film is coated on one side with a medical-grade hypoallergenic pressure-sensitive adhesive of a type well known in the art. In general, acrylic and silicone adhesives have water vapor and oxygen permeabilities that are higher than the thin film materials of choice of this invention. In any case, the moisture vapor and oxygen permeability figures given above should be considered applicable for both thin film adhesive dressings and thin film non-adhesive dressings.

For flexibility and conformability, the film thickness of a dressing embodying this invention should be no greater than 10 mil. Ideally, it should be well under 5 mil. Any of a variety of polymeric compositions can be selected or engineered so that a film of the desired thinness will have moisture vapor and oxygen permeabilities similar to those of a much thicker (70 mil) silicone sheet. For example, a styrene-isoprene block copolymer (Kraton 1107 from Kraton Polymers, Houston, Tex.) may be blended with polyethylene (80% Kraton and 20% polyethylene) to provide a thin film dressing having a thickness under 3 mil that has moisture and oxygen permeabilities similar to those of 70 mil silicone sheeting. Another example is a thin film (under 3 mil thickness) of ethylene-hexene block polymer (Affinity 8200, Dow Chemical, Midland, Mich.). In general, the thin film dressing of this invention may utilize any flexible and conformable polymeric material that is biocompatible and has the required moisture vapor and oxygen permeabilities.

To ensure flexibility and conformability, the material should also be easy to stretch; for example, a material that takes less than 1.5 pounds force per inch of width (1.5 lbf/inch) to stretch to 110% of its original length. This is determined by a tensile test according to ASTM D882, where a one inch width strip of the material is clamped in a pair of jaws that are two inches apart and the jaws are then separated at a rate of 20 inches per minute.

The following Examples compare the critical properties of several thin-film polymeric materials with relatively thick silicone gel sheeting of proven efficacy.

EXAMPLE 1

CHART A

Oxygen Permeability Measurements and Calculations

| Material | Description | Film Thickness (mils) | O2 Transmission Rate Measured (cc/100 in2/day) | O2 Permeability for Material Calculated (cc*mils/100 in2/day) | CicaCare Equivalent Thickness Calculated (mils) |
|---|---|---|---|---|---|
| "CicaCare" (Smith & Nephew, Hull, England) | silicone gel sheeting | 70.0 | 2313 | | |
| "Vector 4111" (Dexco, Houston, TX) | styrene/isoprene block polymer | 3.0 | 2606 | 7844 | 3.3 |
| | | 3.0 | 2414 | 7290 | |
| "Affinity 8200" | ethylene/hexene | 2.2 | 3465 | 7692 | 3.4 |

CHART A-continued

Oxygen Permeability Measurements and Calculations

| Material | Description | Film Thickness (mils) | O2 Transmission Rate Measured (cc/100 in2/day) | O2 Permeability for Material Calculated (cc*mils/100 in2/day) | CicaCare Equivalent Thickness Calculated (mils) |
|---|---|---|---|---|---|
| (Dow Chemical, Midland, MI) | block polymer | 3.1 | 2554 | 7815 | |
| "Kraton 1107 + 0.2 PE (Kraton Polymers, Houston, TX) | styrene/isoprene block polymer (80%) blend with polyethylene (20%) | 3.2 3.0 | 1993 2182 | 6378 6546 | 2.8 |
| "Affinity 8200" + "PSA610" (pressure-sensitive adhesive from General Electric, Schnectady, NY) | adhesive coated film | 2.5 (+ adhesive of about 1 mil) | 2722 | | |
| "Exact 4049" Film (Exxon Corp.) | ethylene/butane block polymer | 2.9 2.9 | 1439 1697 | 4130 4853 | 1.9 2.1 |
| "Exact 4049" + "MD7 4502" adhesive | adhesive-coated film | 2.28 (+ adhesive) | 2388 2441 | | |

CHART B

Water Permeability Measurements and Calculations

| | | Cup Test Method | | | Tewameter Method | |
|---|---|---|---|---|---|---|
| Material | Film Thickness (mils) | MVTR Measured (mg/100 in$^2$/day) | CicaCare Equivalent Thickness Calculated (mils) | Sample Thickness (mils) | TEWL ratio to CicaCare Measured | CicaCare Equivalent Thickness Calculated (mils) |
| "CicaCare" | 70 | 7.1 | | | | |
| "Vector 4111" | 3.0 | | | 3.4 | 0.89 | 3.1 |
| "Affinity 8200" | 2.4 | 4.5 | 1.5 | 2.8 | 0.62 | 1.7 |
| "Kraton 1107" + 0.2 PE | 3.2 | | | 2.7 | 0.89 | 2.4 |
| "Affinity 8200" + "PSA610" | 2.5 (+ adhesive of about 1 mil) | | | | 0.72 | |
| "Exact 4049" Film | | | | 2.7 | 0.62 | 1.7 |

The above charts reveal four different films, and two of these films together with a pressure sensitive adhesive backing, that are relatively thin, well under 5 mil in thickness, and have moisture vapor transmission rates and oxygen permeability comparable to those of a relatively thick (70 mil) silicone gel product. For instance, Vector 4111, a styrene-isoprene block polymer available from Dexco, Houston, Tex., was tested as a film having a thickness of 3.0 mil. At that thickness, its oxygen transmission was 2606 cc/100 in$^2$/day, from which its permeability could be readily calculated (7844 cc*mils/100 in$^2$/day). That reveals that if such a film had an even greater thickness of 3.3 mil, its oxygen permeability would be the same as that of silicone gel sheeting. Since there is no upper limit for the oxygen permeability of a thin film dressing embodying this invention, it follows that a film having a thickness less than 3.3 mil would meet the oxygen permeability requirements of this invention.

Oxygen permeability is only one of the requirements, another being moisture vapor transmission rate. Measurements show that silicone gel sheeting having a thickness of 70 mil (CicaCare) has an MVTR of 7.1 mg/cm$^2$/day. To have a comparable MVTR, a film of Vector 4111 should have a thickness of approximately 3.1 mil. Since 3.1 is well under 3.3, it follows that Vector 4111 having a thickness of 3.1 mil would have an MVTR equivalent to CicaCare and an oxygen permeability even greater than CicaCare.

Measurement of oxygen permeability by the Oxtran Method involves the use of a Mocon 2/20T oxygen permeability test instrument. A sample is placed in the sample chamber where it is held at 37° C. On one side of the sample is a 100% oxygen atmosphere at 50% relative humidity. On the other side, the sample is flushed with a 100% nitrogen carrier gas at 100% relative humidity. The carrier gas moves past an oxygen detector which is used to quantitate oxygen flux through the sample.

The MVTR of test materials is determined using the cup test method in accordance with ASTM E-96-95. Samples are placed over cups containing 10 to 20 ml of saline. The cup is sealed using wax and placed in an environmental oven that is kept at 37° C. and 15% relative humidity. A fan is used to blow air over the sample at a fixed rate as specified in the ASTM method. From measurements of the weight loss of the cup over time, the MVTR through the sample is calculated, such measurements being in units of mg/cm$^2$/day.

Another method for determining water permeability of sheet materials may be used. It involves utilizing a Tewameter TM 210 instrument from Courage and Khazka, of Kolm, Germany. A sample is placed over an aluminum cup and the cup is maintained in contact with a thermostated surface that is kept at 33° C. in the laboratory. After at least one hour of the cup being in contact with the thermostated surface, a Tewameter probe is placed on top of the sample, and a reading is taken, with the water loss rate in the time interval (6 minutes to 6 minutes 30 seconds) being recorded from the instrument display.

This second method may not be as precise as the first method since the environment is not controlled. Such method is used to obtain approximate moisture vapor transmission rate values for thin film materials in comparison with standard silicone gel sheeting, both being evaluated on the same day under essentially the same environmental conditions.

As an example of useful constructs that are easy to stretch, the sample of Exact 4049 film with MD 7-4502 adhesive (Chart A) had a force at 10% strain of 0.33 lbf.

EXAMPLE 2

In the following Chart C, a comparison is made between the transepidermal water loss (TEWL) of an area of normal, uncovered and intact skin with other areas of skin covered by (1) a silicone gel sheeting (CicaCare, Smith & Nephew, Hull, England, 70 mils thickness) and (2) a sample of ethylene/hexene thin film (Affinity 8200, Dow Chemical, Midland, Mich., 2.8 mil). The two samples were placed on skin areas of a human subject in close proximity to an uncovered skin area, with all three areas having been clipped to remove hair prior to the test. The samples were held in place with tape at their edges and were worn by the subject for approximately 18 hours.

TEWL measurements were then made as described in Example 1, second method, utilizing a Tewater TM210 instrument. The measurements were taken directly from each of the skin areas (immediately following removal of each sample), and each was recorded after two minutes of data collection. The results were as follows:

CHART C

| Time of Start of Measurement | Area | TEWL |
| --- | --- | --- |
| 9:32 a.m. | skin that had not been covered | 9.2 |
| 9:37 a.m. | skin previously covered by Affinity 8200 sample | 20.9 |
| 9:40 a.m. | skin previously covered by CicaCare sample | 18.2 |
| 9:45 a.m. | skin previously covered by Affinity 8200 sample | 20.6 |

The TEWL figures are comparative and reveal that the skin area that had not been covered had a TEWL value approximately one-half that of skin previously covered by the CicaCare sample. This reveals that the stratum corneum of the skin covered by the CicaCare sample had become much more hydrated than the uncovered skin area. It will be observed that the TEWL for the area previously covered by the Affinity 8200 sample was similar to, and even slightly greater than, the skin area that had been covered by the CicaCare sample. From this it may be concluded that a 2.8 mil film of ethylene/hexene block polymer (Affinity 8200) is as good or better in hydrating stratum corneum than a relatively thick layer (70 mil) of silicone sheeting (CicaCare).

While in the foregoing, I have disclosed embodiments of this invention in considerable detail for purposes of illustration, it will be understood by those skilled in the art that many of these details may be varied without departing from the spirit and scope of the invention.

What is claimed is:

1. A thin film wound dressing for reducing scars and scar formation, comprising a flexible polymeric film having a thickness no greater than about 10 mil (0.254 mm); said film having an MVTR less than that of human skin and an oxygen transmission rate of at least 300 cc/100 in$^2$/day.

2. The thin film wound dressing of claim 1 wherein said film is stretchable and the load at 10% strain is less than 1.5 pounds force per inch width of film.

3. The thin film wound dressing of claim 1 in which said MVTR is less than 15 mg/cm$^2$/day.

4. The thin film wound dressing of claim 1 in which the MVTR of said film is within the range of 1 to 10 mg/cm$^2$/day.

5. The thin film wound dressing of claim 1 in which said MVTR is within the range of 4 to 8 mg/cm$^2$/day.

6. The thin film wound dressing of claim 1, 2, 3, 4 or 5 in which said dressing contains a bacteriostatic or microbicidal agent.

7. The thin film wound dressing of claim 1, 2, 3, 4 or 5 in which the oxygen transmission rate of said film is at least 600 cc/100 in$^2$/day.

8. The thin film wound dressing of claim 1, 2, 3, 4 or 5 in which the oxygen transmission rate of said film is at least 2000 cc/100 in 2/day.

9. A method of treating healed dermal wounds for reducing scars and their formation, comprising the step of adhering a thin film adhesive dressing to the skin to cover the wound site, said adhesive dressing comprising a flexible polymeric film having a thickness to greater than about 10 mu (0.254 mm); said film being coated on side with a medical-grade hypoallergenic pressure-sensitive adhesive; said film and adhesive coating taken together having an MVTR less than that of human skin and an oxygen transmission rate of at least 300 cc/100 in$^2$/day.

10. The method of claim 9 wherein said film is stretchable and the load at 10% strain is less than 1.5 pound force per inch width of film.

11. The method of claim 9 in which said MVTR is less than 15 mg/cm$^2$/day.

12. The method of claim 9 in which said MVTR is the range of 1 to 10mg/cm$^2$/day.

13. The method of claim 9 in which said MVTR is within the range of 4 to 8 mg/cm$^2$/day.

14. The method of claim 9, 10, 11, 12 or 13 in which said oxygen transmission rate is at least 600 cc/100 in$^2$/day.

15. The method of claim 9, 10, 11, 12 or 13 in which said oxygen transmission rate is at least 2000 cc/100 in$^2$/day.

16. The method of claim 9 in which said adhesive dressing is adhered to a wound site for at least 17 hours per day for a period of at least 8 weeks.

* * * * *

UNITED STATES PATENT AND TRADEMARK OFFICE
CERTIFICATE OF CORRECTION

PATENT NO.    : 6,870,074 B2
DATED         : March 22, 2005
INVENTOR(S)   : Thomas H. Gilman It is certified that error appears in the above-identified patent and that said Letters Patent is hereby corrected as shown below:

Column 8,
Line 13, "wound" should be -- adhesive --;
Line 13, "for reducing scars" should be -- for reducing dermal scars --;
Lines 13-14, "scar formation," should be -- their formation --;
Line 15, after "10 mil (0.254 mm);" insert phrase -- said film being coated on one side with a medical grade hypoallergenic pressure-sensitive adhesive; --;
Lines 15-16, "said film having" should be -- said film and adhesive coating taken together having --;
Lines 17, 21, 23 and 26, "wound" should be -- adhesive --;
Lines 28, 31 and 34, "wound dressing of claim" should be -- adhesive dressing of claims --;
Lines 41, "to greater" should be -- no greater --;
Line 52, "MVTR is the" should be -- MVTR is within the --; and
Lines 56 and 58, "claim" should be -- claims --.

Signed and Sealed this

Twenty-third Day of August, 2005

JON W. DUDAS
*Director of the United States Patent and Trademark Office*